(12) United States Patent
Sippola et al.

(10) Patent No.: US 11,324,519 B2
(45) Date of Patent: May 10, 2022

(54) SURGICAL BURR

(71) Applicant: Surgify Medical Oy, Espoo (FI)

(72) Inventors: Visa Sippola, Helsinki (FI); Seyedshahabaddin Najafi Haeri, Espoo (FI)

(73) Assignee: Surgify Medical Oy, Espoo (FI)

( * ) Notice: Subject to any disclaimer, the term of this patent is extended or adjusted under 35 U.S.C. 154(b) by 0 days.

(21) Appl. No.: 16/340,462

(22) PCT Filed: Oct. 13, 2017

(86) PCT No.: PCT/FI2017/050718
§ 371 (c)(1),
(2) Date: Apr. 9, 2019

(87) PCT Pub. No.: WO2018/069579
PCT Pub. Date: Apr. 19, 2018

(65) Prior Publication Data
US 2019/0307467 A1    Oct. 10, 2019

Related U.S. Application Data

(60) Provisional application No. 62/407,587, filed on Oct. 13, 2016.

(30) Foreign Application Priority Data

Mar. 30, 2017    (FI) .................... PCT/FI2017/050223

(51) Int. Cl.
*A61B 17/16* (2006.01)
*A61C 3/02* (2006.01)
(Continued)

(52) U.S. Cl.
CPC .......... *A61B 17/1617* (2013.01); *A61B 17/14* (2013.01); *A61B 17/142* (2016.11);
(Continued)

(58) Field of Classification Search
CPC .......... A61B 17/1617; A61B 2090/035; A61B 2090/036; A61B 2090/08021; A61C 3/02;
(Continued)

(56) References Cited

U.S. PATENT DOCUMENTS

| 967,805 A | 8/1910 | Meyer |
| 2,455,655 A | 12/1948 | Carroll |

(Continued)

OTHER PUBLICATIONS

International Search Report and Written Opinion, Application No. PCT/FI2017/050718, dated Jun. 20, 2018, 20 pages.

(Continued)

*Primary Examiner* — Kevin T Truong
*Assistant Examiner* — Tracy L Kamikawa
(74) *Attorney, Agent, or Firm* — Ziegler IP Law Group, LLC

(57) ABSTRACT

A surgical burr includes prevention part, a shaft and a working part including at least one cutting or grinding surface for processing of a material selected from a bone, a cartilage, a calcified tissue, a tooth and a foreign object within a patient body. The prevention part is configured to have a first position and a second position. In the first position, it at least partially prevents the cutting or grinding surface from processing the material, when a force applied to the prevention part is less than a predetermined amount of force. In the second position, it allows the cutting or grinding surface to process the material, when the force applied to the prevention part is equal or higher than the predetermined amount of force.

14 Claims, 15 Drawing Sheets

(51) Int. Cl.
*A61B 17/14* (2006.01)
*A61B 90/00* (2016.01)
*A61B 17/00* (2006.01)
*A61C 8/00* (2006.01)

(52) U.S. Cl.
CPC .............. *A61B 17/147* (2016.11); *A61C 3/02* (2013.01); *A61B 2017/00862* (2013.01); *A61B 2090/035* (2016.02); *A61B 2090/036* (2016.02); *A61B 2090/08021* (2016.02); *A61C 8/0089* (2013.01)

(58) Field of Classification Search
CPC ............ B23C 2210/56; B23C 2210/28; B23C 2210/44; B23C 2260/84; B23B 51/0054; B23B 2251/56; B23B 2251/44
See application file for complete search history.

(56) References Cited

U.S. PATENT DOCUMENTS

| | | | |
|---|---|---|---|
| 5,667,509 A | 9/1997 | Westin | |
| 5,876,405 A | 3/1999 | Del Rio et al. | |
| 6,186,787 B1* | 2/2001 | Danger | A61C 3/02 408/226 |
| 7,033,359 B2* | 4/2006 | Meller | A61B 10/025 606/102 |
| 7,914,545 B2* | 3/2011 | Ek | A61B 17/1675 606/180 |
| 8,936,470 B2* | 1/2015 | Pruckner | A61B 17/1626 433/215 |
| 2004/0210229 A1* | 10/2004 | Meller | A61B 10/025 606/80 |
| 2016/0120553 A1* | 5/2016 | Xie | A61B 17/162 606/80 |

OTHER PUBLICATIONS

China National Intellectual Property Administration, First Office Action, Application No. 201780063112.3, dated May 31, 2021, 10 pages.

* cited by examiner

SURGICAL BURR

TECHNICAL FIELD

The present disclosure relates generally to processing of material; and more specifically, to a surgical burr.

BACKGROUND

Conventionally, various devices have been used for shaping of objects, such as cutting, drilling, milling, sawing, polishing and/or grinding. For instance, these devices may include burrs, drill bits, saw blades and cutting disks. Typically, such devices find applications in carpentry, machining, plastics industry and medical sector. Generally, the shaping and processing of the objects require immense control of operator over the hand-held device. Further, targeted action of the device is crucial to minimise unintended damage, especially in medical applications.

The shaping and processing of hard tissues in the medical sector primarily comprises processing of bones or cartilages of a patient undergoing surgery. While soft tissues, such as blood vessels or nerves, can be located in proximity to the processed hard tissue, surgical devices may cause accidental damage to the soft tissues of the patient. For instance, surgical devices may cause damages such as dural tears in spinal surgery, facial nerve paralysis during ENT surgery (ear-nose-throat surgery) or lingual nerve paralysis during dental procedures. Subsequently, the damage to the soft tissues may cause swelling, pain, numbness, bleeding and several other complications. Additionally, the damage to the soft tissues may prolong the recovery of the patient.

One possible tool used to perform a surgical procedure is a burr. A burr generally consists of a head formed from rigid material, typically metal and tungsten carbide. There typically exists two types of burrs, cutting burrs and grinding burrs. A cutting burr has a head shaped to have a number of flutes. The flutes are formed to define tissue cutting edges, and each flute has a rake surface and a clearance surface. The rake and clearance surfaces meet to form a cutting edge that extends along the length of the flute, as is shown in more details in the Figures below. In other words, the rake surface is a face in front of the cutting edge which shaves the material and the clearance surface is the surface behind a cutting edge which extends toward an adjacent flute. A grinding burr has a head having a surface typically coated with an abrasive coating, such as diamond or hard carbon coating.

Furthermore, in a burr, a shaft extends rearwardly from the head. The free end of the shaft has a feature that facilitates locking the shaft to a powered handpiece. The actuation of the handpiece results in the rotation of the burr. During a surgical procedure, the burr head is placed against a surgical site where a section of tissue is to be removed, i.e. processed. The rotating cutting edges typically excise tissue away from the surgical site, while the burrs can also be used for processing foreign objects, such as implants, within the body. Burrs of various shapes and sizes are used in procedures such as orthopedic surgery, neuro and spinal surgery, ear, nose and throat surgery and in other surgical procedures in which a sub-procedure is to selectively remove a section of tissue.

In patent document U.S. Pat. No. 5,876,405, titled "Perforator", there is described a drill bit with a centrally disposed sharp guide pin to penetrate a material (such as, a bone structure), while the drill bit is a hollow cylindrical wall with cutting edges formed in its bottom end to remove/cut a bone plug after drilling is complete. Therefore, the document does not provide a method to prevent unintended drilling of material by the sharp cutting edges of a conventional twist drill bit, which are located at the tip of the drill bit.

A burr is thus different from a hollow drill bit, as having a head in burrs differentiates it from such hollow drill bit. A hollow drill bit has cutting edges in its bottom side, which is not the case for a burr. In a twist drill bit, spiral flutes are ground in to the body of the shaft, and the flutes at the tip form cutting edges on the bottom end, not on the circumference of the drill bit. In a burr, in case there are flutes, they form cutting edges on the circumference of the burr head. Furthermore, the geometry and application of drills and burrs are substantially different. Burrs are used for milling and grinding, i.e. removing material with a rotary cutter from a workpiece by advancing in any direction (as cutting occurs on the circumference of the burr), while drill bits are used for drilling, i.e. removing material along their rotation axis (as drilling occurs at the bottom end of the drill bit). A further difference is that a burr removes material from a material to be processed, instead of making a hole into the material as a drill bit does.

In recent past, advances have been made to improve surgical devices such as high-speed drills and ultrasonic cutting devices. However, there has not been a substantial change in the surgical devices to minimise unintended damage to the surrounding tissues. For example, the risk of damaging soft tissues during the processing of hard tissues is still prevalent. Additionally, the ultrasonic cutting devices require purchasing completely new equipment and also require training of a new type of surgical procedure, which is inconvenient for the user.

Various industrial tools such as table saws or disc cutters may present a risk for the user, such as for the user's fingers or hands. Different protection means exists, but it may still be beneficial to try to improve these safety devices.

Therefore, in light of the foregoing discussion, there exists a need to overcome the aforementioned drawbacks associated with conventional devices for processing of object.

SUMMARY

The present disclosure seeks to provide a surgical burr for processing of a material. The present disclosure also seeks to provide a solution to the existing problem of unintended damage caused to soft tissues during processing of hard tissues. An aim of the present disclosure is further to provide a solution that overcomes at least partially the problems encountered in prior art, and provides a safe, precise and reliable burr to achieve better control, safety and targeted action for processing of a material in medical applications. A still further object is to decrease chattering of the burr when in use.

In one aspect, an embodiment of the present disclosure provides a surgical burr comprising
  prevention means;
  attachment means; and
  a working part comprising at least one working means for processing of a material selected from a bone, a cartilage, a calcified tissue, a tooth and a foreign object within a patient body, wherein the working means is selected from a grinding surface and flutes defining cutting edges;

wherein the prevention means is configured to have
a first position in which it is arranged to at least partially prevent the working means from processing the material, when a force applied to the prevention means is less than a predetermined amount of force, and
a second position in which it is arranged to allow the working means to process the material, when the force applied to the prevention means is equal or higher than the predetermined amount of force.

Embodiments of the present disclosure substantially eliminate or at least partially address the aforementioned problems in the prior art, and enables safe and targeted processing of a material.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
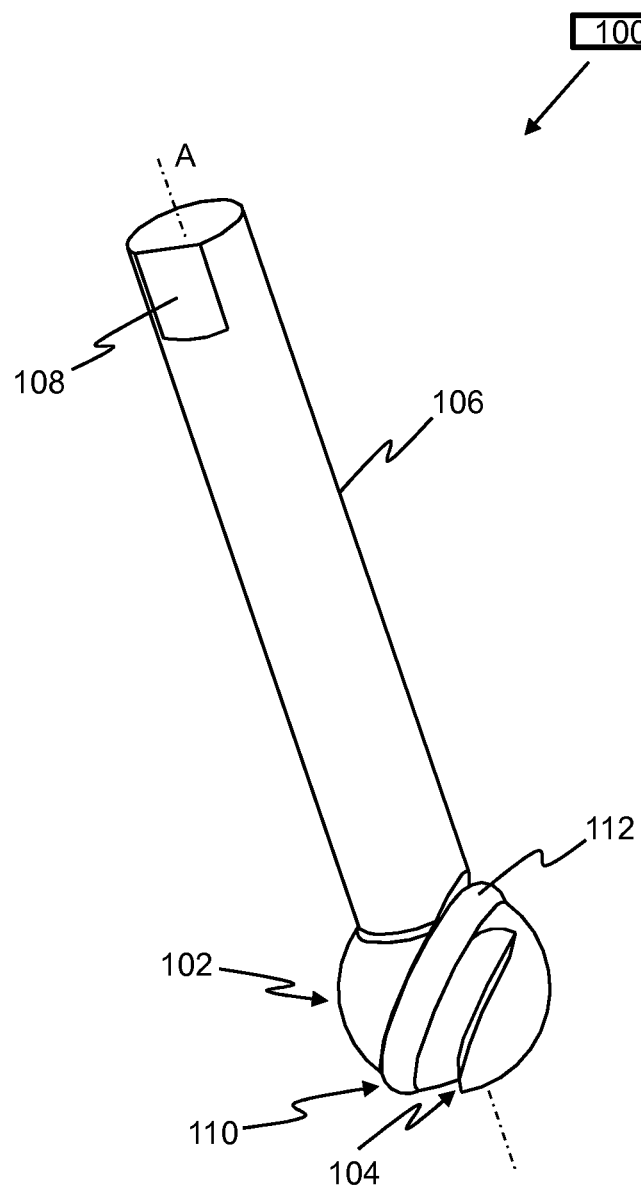
FIGS. 1, 2, 3, 4 and 5 are different views of a surgical burr, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a surgical burr comprising
prevention means;
attachment means; and
a working part comprising at least one working means for processing of a material selected from a bone, a cartilage, a calcified tissue, a tooth and a foreign object within a patient body, wherein the working means is selected from a grinding surface and flutes defining cutting edges;
wherein the prevention means is configured to have
a first position in which it is arranged to at least partially prevent the working means from processing the material, when a force applied to the prevention means is less than a predetermined amount of force, and
a second position in which it is arranged to allow the working means to process the material, when the force applied to the prevention means is equal or higher than the predetermined amount of force.

The present disclosure provides a surgical burr for processing of material. A primary advantage of the device is that when used to process hard tissue, adjacent soft tissues are protected, thanks to the prevention means. Indeed, the device substantially lowers the risk of processing of unintended objects adjacent to the object undergoing processing, such as soft tissue adjacent to a hard tissue being processed (for example drilled). The device also enables an operator to exercise better control over the processing of the object. Indeed, the prevention means significantly increases the controllability as it prevents the cutting tool from unwanted and/or excessive penetration to the work material. In other words, it does not allow a sudden penetration of the tool to the work material. When that happens, the tool starts to aggressively vibrate (called chattering) and sometimes the tool goes out of control (jumping). Besides that, the prevention means allows the operator to adjust the depth of cut according to the amount of the pushing force he/she applies. This increase the precision of cut. Consequently, the device achieves precise processing on a desired portion of the object. Therefore, a device which relates to a medical sector, provides safer operation and significantly reduces risk of soft tissue damage in surgical operations. Also, the device enables processing of the object in a time efficient manner. Additionally, the device is adaptable according to the type of processing the object requires, i.e. adaptable to conventional and existing shaping and processing devices, irrespective of their type. Indeed, the "shaping and processing" in this specification relates to all kinds of working of hard tissues, such as cutting, grinding, milling, drilling, polishing, sawing and so on, while in connection with the embodiment of a surgical burr, processing means cutting, milling and grinding. Furthermore, in this specification, the term "working surface" relates to the part of the working part that actually processes the object, and it can be only a part of the working part or in some cases, the whole of the working part can be the working surface.

The present disclosure provides a surgical burr that can be made in several different manners, some of which are explained in more detail below. A main feature of the device is that the prevention means has two different positions, a first position and a second position. In the first position, the prevention means protrudes from the working part to at least partly, preferably fully, prevent the working means from processing the material. This first position is the one the prevention means takes when a force applied to it is less than a predetermined amount of force. This means that the user will need for example to press the device against the material to be processed in order to start the processing, i.e. to overcome the limit of force required. The second position of the prevention means is the position in which it retracts to allow the working means to process the material. This position is taken by the prevention means when the force applied to it is equal or higher than the predetermined amount of force. The predetermined amount of force thus forms a limit which defines the position of the prevention means. The prevention means may be actioned into its first position by an attachment means, for example by means of an inner part, centrifugal forces, or the outer part deformation (elastomeric or flexible moving part). These different embodiments will be explained in more detail below.

The surgical burr comprises prevention means for preventing the working means from processing the material. The prevention means is thus a mechanism, that can have one or more parts. For example, the prevention means may consist of an outer moving part and an inner spring (for example a canted coil spring or an elastomer functioning as a spring). Alternatively, the prevention means may consist of a moving part which has an outer and an inner portion (for example an integrated spring and ring), either as integral parts or as separate parts. Still further, the prevention means may consist of a resilient part attached to an outer surface of the working part, for example flaps or elastomeric sections. In this context, by the term resilient are meant parts made of a material that is capable of changing shape, for example by bending or compressing under force (such as pressure) and to return to its original shape once the force is no longer applied on the part.

According to an embodiment, the prevention means is arranged to protrude from the working part in its first position and to retract from the working means in its second position. According to another embodiment, the prevention means is arranged, in its first position, to push soft tissue away from the cutting edge, and, in its second position, to allow the working means to be in contact with hard tissue.

The prevention means is/are thus configured to have two different positions depending on the force applied to the prevention means, when the working part is interacting with the material to be processed. There are different forms of relevant forces, such as friction, normal force and shear force. By force we mean normal force applied to the prevention mechanism at the contact point between outer surface of prevention means and the material (which is the reaction of the material to the pushing force applied by the user and the motor torque). The force may thus be the contact force.

According to an embodiment, the working part comprises at least one indentation into which the prevention means can retract, i.e. for arranging the prevention means therein. In this embodiment, the prevention means is partially arranged in the indentation when it is in its first position, and essentially fully arranged therein, when the prevention means is in its second position. According to another embodiment, the indentation is a groove or a hole in the working part. Such an embodiment is preferably used when the prevention means is arranged on the same level of the working part as the working means, such that the prevention means retracts into the indentation to allow the working means to process the objects. According to an embodiment, the indentation has a V-shape or a stepped shape profile. By V-shape it is meant that the width of the indentation at its bottom is smaller than the width of the indentation near the surface of the working part. By stepped shape profile it is meant that the width of the indentation is not uniform but rather it has different widths and the changes in width are not continuous but sharp. Such stepped shape profile allows only limited radial movement of the prevention means (in the form of a ring or partial ring, for example) related to the working part.

This description concerns mainly a surgical burr. However, the same principle is fully applicable to twist drills and saws used in surgery. Thus, the various embodiments and alternatives described herein are fully applicable to the twist drills and saws as also explained in this description. Therefore, the term working means of the surgical burr is equivalent to the term working surface when the surgical twist-drill and/or surgical saw are used. Likewise, the terms material and object can be interchanged when it is question of what the device described is aimed to process.

In other embodiments, such as when a saw is used, no indentation is needed as the prevention means can be arranged on top of the working part such that it is essentially parallel to it. Indeed, in such a case, the working surface is for example the teethed side surface of the saw, and the prevention means is arranged to at least partly cover that surface when it is in its first position. By covering it is here meant that when the device is looked at from above or below, the cutting surface (the teeth) are not fully visible.

According to an embodiment, the present description relates to the device comprising prevention means; attachment means; and a working part comprising at least one working means (or, at least one working surface) for the processing of a material (or, an object) and at least one indentation for arranging the prevention means therein. The prevention means is configured to protrude from the working part when a force applied to the prevention means is less than a predetermined amount of force, and retract to the at least one indentation when the force applied to the prevention means is equal or higher than the predetermined amount of force.

The different parts of the device can be connected to each other in different ways. For example, there might be a prominent part on the inner surface of the prevention means, which rests against the indentation and acts as pivot point. A spring installed at one end of the prevention means applies the required force to protrude the prevention means from the indentation to provide protection during use of the device.

According to an embodiment of the invention, the prevention means may also have more than two positions, i.e. intermediate positions between the first position and the second position. These intermediate positions (which can be in any discrete number, such as one, two, three, four or five) are used to control the depth of the cut. Indeed, for example a first intermediate position allows a depth of 1 µm (micrometer) per revolution for the cut, while a second intermediate position allows a depth of 2 µm per revolution for the cut, and the third position allows a depth of 3 µm per revolution for the cut. These positions are selected by the user with the force applied to the device and thus the force the device is pushed against the material under processing and can be achieved with various technical means, such as spring. There may also be different limitation means in the device, that lock the prevention means into the selected intermediate position, and a slightly higher force is needed to overcome the lock and to move to a next position. It is also possible to design the device in such a manner that when pressure (i.e. the contact force) is released, the prevention means automatically returns to its first position.

Depending on the flexibility of the prevention means, the retraction to the indentation might happen in forms of deformation of the (flexible) prevention means, lever type movement of the (rigid) prevention means, or a combination of them (semi-flexible prevention means). Hence, the existence of a spring (as described below in connection with one embodiment) might not be crucial when the prevention means is a spring itself or is made of an elastomer. The spring may thus be made for example of silicone, or it may be a canted coil or a wave spring. In addition, the prevention means may be configured to have a hook shaped form at the end, to allow only limited radial movement of the prevention means in relation to the working part.

The prevention means may be made in one part or it may be made in several parts, such as an inner part and an outer part (or several of either or both), as explained in more detail below. The shape of the prevention means may also vary, depending on the working surface, for example. The prevention means may also be in one part while having the same form as a prevention means in two parts, as the inner and outer parts can be made integral with one another.

In an implementation of the present disclosure, the device is a surgical burr. The surgical burr comprises a working part comprising at least one working means for the processing of a material. The material is selected from a bone, a cartilage, a calcified tissue, a tooth and a foreign object within a patient body (such as an implant). In an embodiment, the surgical burr may be a burr suitable for cutting, milling, polishing and/or grinding. For instance, the surgical burr may be used for performing surgical operations for the treatment of various pathologies, injuries, disabilities, bone misalignments or dental conditions.

In an embodiment, the device, such as the surgical burr, may be attached to a rotating mechanism using an attachment means. For example, the rotating mechanism may be powered by a motor, which may be coupled to the device using a coupling means, such as a chuck, a bearing and a gear arrangement. In one embodiment, the rotating mechanism may provide a rotary motion to the device. In another embodiment, the rotating mechanism may be adapted to provide an oscillatory motion to the device. For example, the rotating mechanism may be associated with a suitable motion changing mechanism (a gear arrangement) that converts a rotary motion into the oscillatory motion.

In an embodiment, the working means for processing of the material is selected from a cutting surface or a grinding surface (also called abrasive surface). Specifically, each configuration of the working part may process the material differently according to requirement of operator of the surgical burr. The working part may also comprise more than one type of working means, if need be.

In an embodiment, the surgical burr may comprise a working part attached to a shank. Specifically, the working part is a spherical body configured for cutting, grinding and shaping of work material such as bones or teeth. Naturally, the working part may also have other shapes, such as cylindrical shape, egg-like shape, pear-like shape, conical shape etc. The present device is also usable for other materials than hard tissues, such as wood, metal or ceramics. More specifically, the at least one working means of the surgical burr may be a protruding or an elevated surface on the spherical body, which may act as a cutting surface, a grinding surface or an abrasive surface etc. Further, the working part may be attached to a shank. The shank is operable to be attached to the rotating mechanism to provide rotary motion to the working part, through the attachment means designed in for example the shank of the surgical burr. Subsequently, the rotation of the working part of the surgical burr enables removal of material from the surface of the work material. In an example, the surgical burr may be configured to rotate in the range of hundreds or thousands (for example 1,000-4,000,000) of revolutions per minute for effortless removal of material from the surface of work material. In an example, the surgical burr may be used to shape or remove bone to treat conditions of the head or spine.

The prevention means is configured to protrude from the working part when a force applied to the prevention means is less than a predetermined amount of force and to retract when the force applied to the prevention means is equal or higher than the predetermined amount of force. In an embodiment, the predetermined amount of force is associated with (or based on) the composition of a material to be contacted by the working means for the processing thereof. Specifically, the material (or composition thereof) may be hard enough to provide a force (equal or higher than the predetermined amount of force) when the prevention means is allowed to contact and press against the object. Therefore, if the prevention means is allowed to contact and press against a material having a soft composition, the prevention means may not retract. Alternatively, if the prevention means is allowed to contact and press against a material having a hard composition, the prevention means may retract.

In an embodiment, the predetermined amount of force is selected to prevent the processing of a secondary material, when the secondary material is softer than the material. As explained herein above, the secondary material may include a soft composition. For example, the secondary material may be soft tissue such as a blood vessel or nerve tissue; and the material may be a bone or a tooth. Therefore, the force, exerted on the prevention means upon contact therewith, may be equal to or higher than the predetermined amount of force when the prevention means is allowed to contact and pressed against hard tissues such as bone or teeth.

According to an embodiment, the working part of the surgical burr may come in contact with the material to enable processing thereof when the prevention means retracts, optionally to the at least one indentation. Further, prevention means is operable to at least reduce the surface contact between the working part and soft tissues to avoid any unintended damage to the soft tissues thereof. In an example, the soft tissues such as nerves, blood vessels, and so forth may be located near the hard tissues such as bones and cartilages in human body. The soft tissue to be protected may be also the user's fingers or the material to be processed may be hard material such as a workpiece.

In an embodiment, the prevention means may comprise at least one outer member and at least one inner member. In yet another embodiment, the prevention means comprises at least one outer part and at least one inner part, i.e. the inner and outer members are integral with one another. Thus, all the various embodiments and designs described with respect to the inner and outer members apply mutatis mutandis to the inner and outer parts.

In an embodiment, the inner member may be made of an elastomer and arranged in the at least one indentation between the working part and the outer member. The outer member may be a ring. According to an embodiment, when the device is a surgical burr, the outer member is a ring. Further, in such embodiment, the indentation may be a circular groove in the working part of the burr. Specifically, the indentation may be a groove in a spherical surface of the surgical burr. Also, a plane of the groove may be tilted at an angle as compared to central axis of the shank of the surgical burr, in order to provide protection all around the working part when it rotates about the axis of rotation. Further, the groove may be designed to limit the radial movement of the ring on the spherical surface of the burr. For example, the groove may be configured to have a V-shape or a stepped shape profile, which may only allow limited radial movement of the ring related to the working part.

In one embodiment, the ring has an opening arranged to be in contact with a notch in the working part for preventing the ring to rotate in relation to the working part. Specifically, core of the burr may be configured to have an additional piece of material attached inside a groove. Therefore, such protruding element may prevent the ring to rotate in relation to the working part. Furthermore, the notch may be arranged to fit into the opening of the ring. Therefore, the notch restricts relative movement of the ring to rotate in relation to the working part. This enables in precluding damage that may be caused by the relative movement of the ring to the inner member, particularly, elastomeric surface of the inner member. Likewise, the ring may have a protrusion arranged to be in contact with a notch in the working part for preventing the ring to rotate in relation to the working part. Still further, a closed ring can be used, where the ring is compressed to a specific shape and its ends are attached to one another to form a loop. The attaching can be done for example by laser welding.

In an embodiment, the inner member is a spring arranged between the working part and the outer member, for example in the at least one indentation. That is, the inner member (for example an elastomer) is configured to act as a spring. Specifically, the inner member is adapted to compress and expand, when subject to or released from equal to or more than the predetermined amount of force. Further, the dimensions and stiffness or composition of the inner member are selected in such a manner that the outer member protrudes at least partly from the working part when the force applied to the prevention means is less than a predetermined amount of force, and the outer member retracts into the at least one indentation when the force applied to the prevention means is equal or higher than the predetermined amount of force. In an embodiment, the inner member (for example the elastomer) may comprise cuts or slices on an outer surface thereof to provide enough space, which allows compression of the inner member. In another embodiment, the inner member may be a circular canted coil spring. Specifically, such spring may be closed loop that is stretched to be installed in the at least one indentation in the working part. In yet another embodiment, the inner member may be a circular wave spring. Furthermore, such spring may be welded to the inside of the at least one indentation in the working part or to the outer member.

According to an embodiment, the outer member (for example the ring) is configured to protect the soft tissues from unintended processing. Specifically, the inner member may undergo compression when the ring is pressed against a hard tissue such as teeth or bones to expose the outer surface of the working part of the surgical burr. Alternatively, the inner member may not undergo compression when the outer member is pressed against the soft tissues to prevent unintended contact between the working part of the surgical burr and the soft tissues.

In another embodiment, the prevention means may comprise an elastomer arranged in multiple indentations in the working part of the surgical burr. Further, the indentations may be in the form of segments on opposite sides of the surgical burr in which the elastomer may be arranged. The elastomer in the segments is configured to protrude or retract depending upon the force applied thereto. Alternatively, the surgical burr may have cutting edges in shape of flutes (i.e. the working means) in the working part of the surgical burr. The elastomer may be arranged in the alternate flutes thereof. Further, the elastomer may retract to the flutes (when subjected equal to or more than predetermined amount of force) to expose the cutting edges of the surgical burr to enable processing.

According to an embodiment, the prevention means is a moving part having an outer portion and inner portion, and the outer portion is configured to protrude from the working part to prevent the working surface from processing the material, when the prevention means is in its first position. Indeed, in this embodiment, the inner portion is configured to act as a spring, wherein the spring constant is dimensioned so that the outer portion protrudes at least partly from the working part when the force applied to the prevention means is less than a predetermined amount of force, and the outer portion retracts into the at least one indentation when the force applied to the prevention means is equal or higher than the predetermined amount of force.

In an embodiment, the working means are cutting edges and the prevention means comprises a number of flaps, each flap being arranged between two cutting edges. In this case, each flap is arranged, in its first position, to push soft tissue away from the cutting edge, thus preventing the cutting edge from touching the soft tissue. Therefore, each flap is arranged, in its second position, to allow the working means to be in contact with hard tissue.

In another embodiment, the working part of the surgical burr may be cylindrical in shape. In this embodiment, the working means are cutting edges on the cylindrical surface and the prevention means comprises a number of flaps, each flap being arranged between two cutting edges. In this case, each flap is arranged, in its first position, to push soft tissue away the cutting edge, and, in its second position, to allow the working means to be in contact with hard tissue. The flaps can be made from metal or plastic, for example from a thin sheet of stainless steel.

Thus, as mentioned above, the surgical burr may be attached to a rotating mechanism using the shank attached to the working part. Furthermore, the working part may comprise cutting edges on a surface of the working part. Additionally, the prevention means may be arranged between the cutting edges of the working part. Specifically, the prevention means may be resilient flaps arranged between the cutting edges. More specifically, the resilient flaps may be attached from a first end using spot or laser welding to the working part. Furthermore, in case of a plastic flaps, the resilient flaps may be attached using an adhesive. Alternatively, the working part may have a slot or similar into which an end of the flap or a protrusion (such as a rail) at one end of the flap can be arranged. In operation, the prevention means may push soft tissue away from the cutting edge, when the force applied thereto is less than the predetermined amount of force, thus preventing the cutting edge to come into contact with the soft tissue. Additionally, the prevention means may retract and is pressed against the working part when the force applied thereto is equal or higher than the predetermined amount of force.

In an embodiment, the prevention means, such as the resilient flaps, arranged between the cutting edges of the surgical burr may have a filler arranged on a second edge of the resilient flap. Specifically, the filler member may be an elastomeric member that may be compresses to allow retraction of the prevention means. Furthermore, the filler member may prevent accumulation of the processed material behind the resilient flaps. In yet another implementation of the present disclosure, the device is a twist-drill. The twist-drill is a cylindrical tool having a working part comprising at least one working surface for drilling of an object. Further, the twist-drill may include be attached to a rotating mechanism using an attachment means (such as, a shank) to enable the twist-drill for drilling of the object.

In an embodiment, the at least one working surface may be at least one cutting edge in the bottom end, and one flute for drilling of the object. In another embodiment, when the device is a twist-drill, the at least one indentation may be a hole in the working part. Specifically, the indentation is a longitudinal hole in the working part in proximity of the cutting edge of the drill bit for arranging the prevention means therein. In an embodiment, the indentation may comprise more than one hole in the working part of the drill bit for arranging more than one prevention means therein.

In an embodiment, the at least one prevention means comprises at least one outer member and at least one inner member, and the inner member is in the form of a spring. Specifically, the at least one inner member and the at least one outer member may both be configured to be arranged in the at least one indentation in the working part (such as, a hole), configured at the bottom end of the twist-drill. In one embodiment, the at least one outer member may look like a hook, i.e. it may have a stem and a hooked tip. Further, the at least one outer member may be mounted within the hole. For example, the at least one outer member may include a protruding part or a stop adapted to be received by a recess around the hole, such that at least one outer member does not come out of the hole. Alternatively, the at least one outer member may be coupled to the at least one inner member, and the at least one inner member may be further coupled to the hole, for example using a suitable adhesive. The at least one inner member is arranged in the hole between the twist-drill and the at least one outer member. In an embodiment, the at least one prevention means of the twist-drill, may include a pair of holes, each accommodating the at least one inner member and at least one outer member therein.

According to the embodiment, the inner portion may be a helical spring, and the spring is dimensioned so that the outer portion protrudes at least partly from the working part when the force applied to the prevention means is less than a predetermined amount of force. Further, the outer portion retracts into the at least one indentation when the force applied to the prevention means is equal or higher than the predetermined amount of force. Specifically, the outer portion may compress the inner portion, when pressed against hard tissues, such as bones, to expose the cutting edges of the twist-drill. Therefore, the outer portion prevents unintended contact between the at least one working surface and the soft tissues. Specifically, if the at least one working surface comes in contact with the soft tissue (or moved away from the hard tissue), a tip of the outer member may protrude due to lack of predetermined force and thereby prevent damage to the soft tissue.

In another aspect, an embodiment of the present disclosure thus provides a twist-drill comprising
  at least one prevention means;
  attachment means; and
  a working part comprising at least one working surface for drilling of an object;
wherein the at least one prevention means is configured to have
  a first position in which it protrudes from the working part, to prevent the working surface from drilling the object, when a force applied to the prevention means is less than a predetermined amount of force, and
  a second position in which it retracts to allow the working surface to drill the object, when the force applied to the prevention means is equal or higher than the predetermined amount of force.

In this embodiment, the working surface is located on a bottom end of the drill bit. I.e. the drill bit is attached to a drill from one end and the working surface, in this case cutting edges, are arranged in the other end, i.e. bottom end.

In yet another aspect, an embodiment of the present disclosure provides a saw as mentioned above. Such saw comprises
  prevention means;
  attachment means; and
  a working part comprising at least one working surface for cutting of an object, in the form of working teeth;
wherein the prevention means is configured to have
  a first position in which it protrudes from the working part, to prevent the working surface from cutting the object, when a force applied to the prevention means is less than a predetermined amount of force, and
  a second position in which it retracts to allow the working surface to cut the object, when the force applied to the prevention means is equal or higher than the predetermined amount of force.

In yet another implementation of the present disclosure, the device may thus be a saw. Further, the working part of the saw may comprise at least one working surface for cutting of an object, in form of working teeth. Furthermore, the working part may be attached to an attachment means, optionally integral with the saw, adapted to be operatively coupled to a rotating mechanism to provide oscillatory motion to the saw.

Optionally, the saw is selected from a reciprocating saw blade, a circular saw blade and an oscillating saw blade. In an embodiment, the saw may be an oscillating saw blade or a reciprocating saw blade. The oscillating saw blade may comprise an indentation on the surface thereof. Further, the prevention means may be arranged in the indentation on a surface, of the oscillating saw blade, adjacent to working teeth. Furthermore, an inner member of the prevention means may be a spring that may be placed in the indentation to control protrusion and retraction of an outer member of the prevention means with respect to the indentation. The spring may be thus made of an elastomeric part or it may be a traditional metallic spring. In an embodiment, the outer member may be a comb like structure configured to protrude in between working teeth of the oscillating saw blade. The outer member is configured to prevent unintended contact between the working teeth and soft tissues. Further, the outer member of the prevention means may retract to the indentation, when the outer member is subject to hard tissue, and thereby exposing the working teeth of the oscillating saw blade to the hard tissue. In these embodiments, it is also possible to design the device without indentations on the working part, as has been described above.

According to an embodiment, the saw may be a circular saw blade. Further, the circular saw blade may include a central mounting hole, adapted to be operatively coupled to a rotating mechanism, using an attachment means to obtain rotary motion. Further, prevention means may be arranged in at least one indentation present on either one or both sides of the circular saw blade, and/or in the middle of the circular saw blade. The prevention means may comprise for example two separate semi-circular outer members on at least one side of the circular saw blade. The semi-circular outer members are configured to protrude from the lateral surface of the circular saw blade, i.e. to at least partly cover the sharp edges of the working teeth.

In one embodiment, the prevention means also includes an inner member, such as a pair of elliptical spring members, positioned between the outer members on at least one side of the circular saw blade. The springs may be configured to push the moving part(s) outwards or pulling it (them) inwards. For example, at the high rotations, centrifugal forces are so high that the force required to retract the moving parts inside the indentation is too high for practical purposes. In this case the tension spring is needed to reduce the force at the high operating speed. Specifically, the semi-circular outer members on each side of the cutting disk may have a common inner member to control the protrusion and retraction of the outer members with respect to the indentation. Moreover, the protrusion and retraction of the outer members with respect to each quadrant is configured separately. Thus, the circular saw blade is operable to perform cutting of the object and simultaneously protect the secondary object surrounding the object (for example soft tissue adjacent to hard tissue or user's finger or hand). Additionally, the semi-circular outer members of the prevention means may be supported by support tabs configured in the indentations on the surface of the circular saw blade. The number of support tabs can be for example one, two, three, four, five or six. Each support tab typically comprises a head and a shaft and they are arranged by press fitting into the holes arranged in the circular saw blade. Further, the common inner member on each side of the circular saw blade may be supported between the semi-circular outer members with help of the support tabs, more specifically the shafts of the support tabs. Therefore, the prevention means on each side of the circular saw blade may be configured to protect alternate quadrants of the working teeth from unintended contact with the secondary object.

The arrangement of working teeth described above can have different structures. For example, the working teeth can be divided into four sets of working teeth. These sets of working teeth can protrude from a middle plane, in opposite directions, depending on the position of the moving part adjacent to it. The number of working teeth sets may depend on the number of moving parts. Typically, the circular saw blade is configured to be capable of making cuts as wide as the blade width. If the moving parts are placed in a same plane, the cutting penetration is limited as the moving parts do not have the capability of removing material ahead of them.

As has been described, the present device can have various forms. One additional possible form is a reciprocating saw blade, in which the cutting action is achieved through a push-and-pull ("reciprocating") motion of the blade. The blades of such reciprocating saw may be arranged in any suitable manner, for example as describe above in connection with the oscillating saw blade. A still further possibility is any kind of burr, having various forms, some of which are illustrated below in connection with the Figures.

According to an embodiment, the object to be processed by the device (of the present disclosure) may include different compositions. For example, the object may be made of a material selected from a bone, a tooth, cartilage, a calcified tissue, a crust, a wood, a metal, a plastic. Specifically, the device of the present disclosure may be operable for processing of object in carpentry, metal machining and plastics industry. Further, the crust may be a hardened layer, a deposit or a coating on the surface of an object. The device may be used for the processing of the crust on the surface of the object. Additionally, the device may be used in large-scale applications such as carpentry and metal machining to achieve better control for handheld devices, targeted processing and minimal damage of objects such as wooden planks, metal sheets, and so forth.

DETAILED DESCRIPTION OF THE DRAWINGS

Referring to FIG. 1, illustrated is a perspective view of a surgical burr 100, in accordance with an embodiment of the present disclosure. As shown, the surgical burr 100 comprises a working part 102 having at least one working means 104. Furthermore, the working part 102 is spherical in shape. The working part 102 is attached to a shank 106.

The shank 106 comprises attachment means 108 at its other end, to allow the shank 106 to receive the rotary motion. Further, the working part 102 includes a prevention means 110. Moreover, the prevention means 110 includes an outer member 112, in this embodiment a ring. The surgical burr 100 is a cutting burr and the working means 104 are cutting edges. Furthermore, the axis A illustrates the axis for rotational motion of the surgical burr 100.

Figure 2:
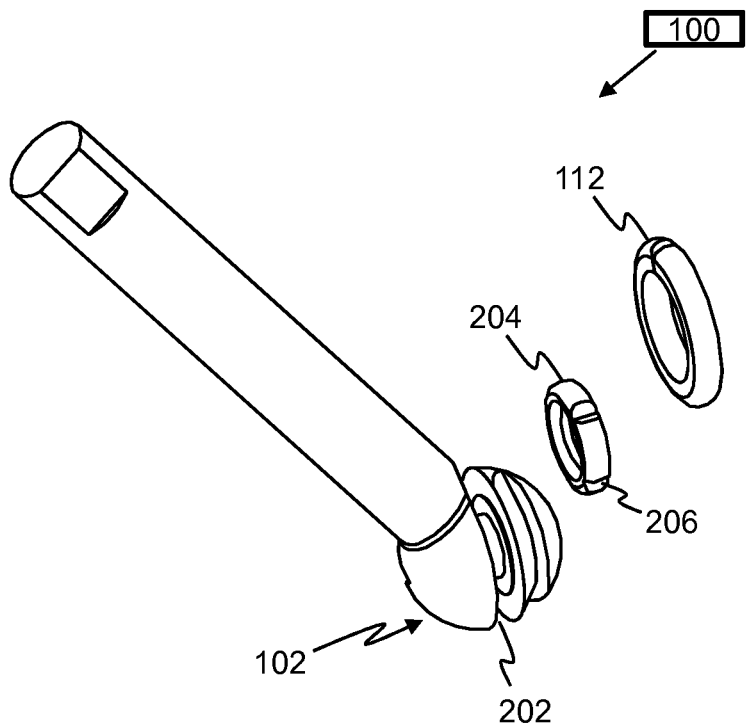

Referring to FIG. 2, illustrated is an exploded view of the surgical burr 100 of FIG. 1, in accordance with an embodiment of the present disclosure. As shown, the working part 102 comprises at least one indentation 202 for arranging the prevention means therein. The prevention means comprises the outer member 112 and the inner member 204. Optionally, the inner member 204 is made of an elastomer and arranged in the at least one indentation 202 between the working part 102 and the outer member 112. The inner member 204 includes cuts 206 on an outer surface of the inner member 204.

Figure 3:
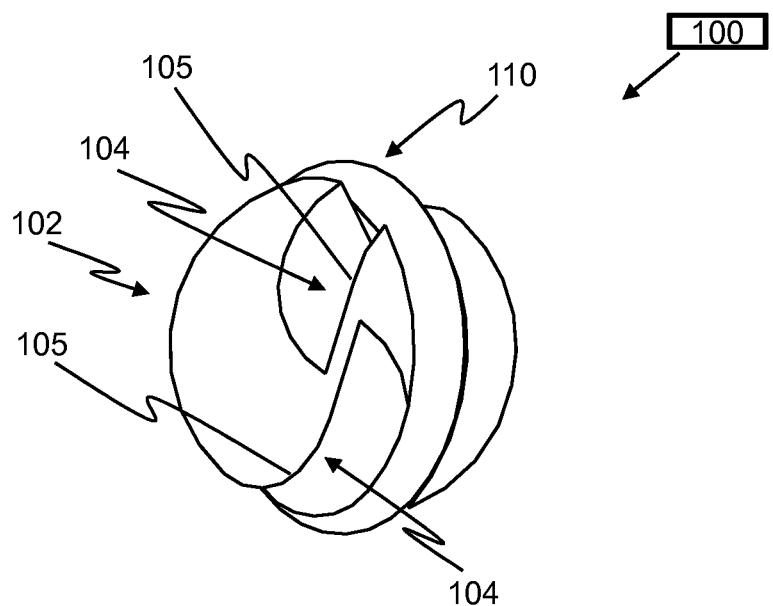

Referring to FIG. 3, illustrated is a bottom view of the surgical burr 100, in accordance with an embodiment of the present disclosure. As shown, the working part 102 comprises working means 104, such as the cutting edges 105. Furthermore, the prevention means 110 is arranged on the working part 102.

Figure 4:
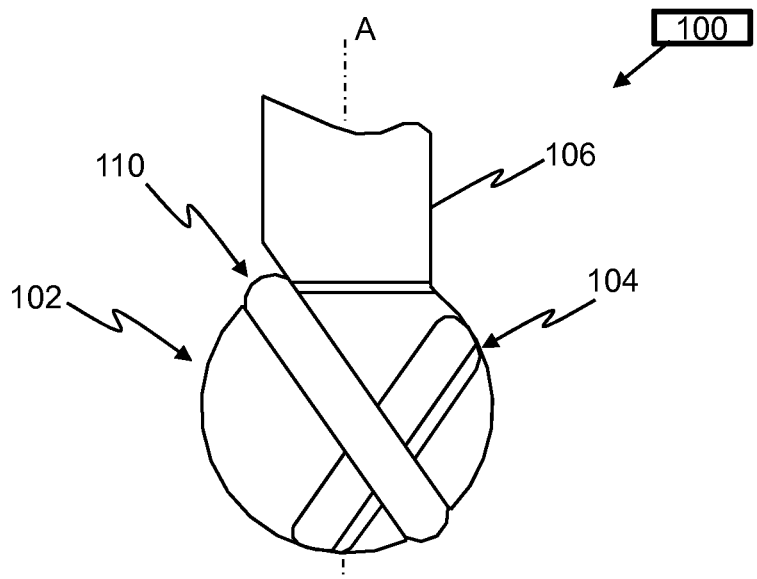
Figure 5:
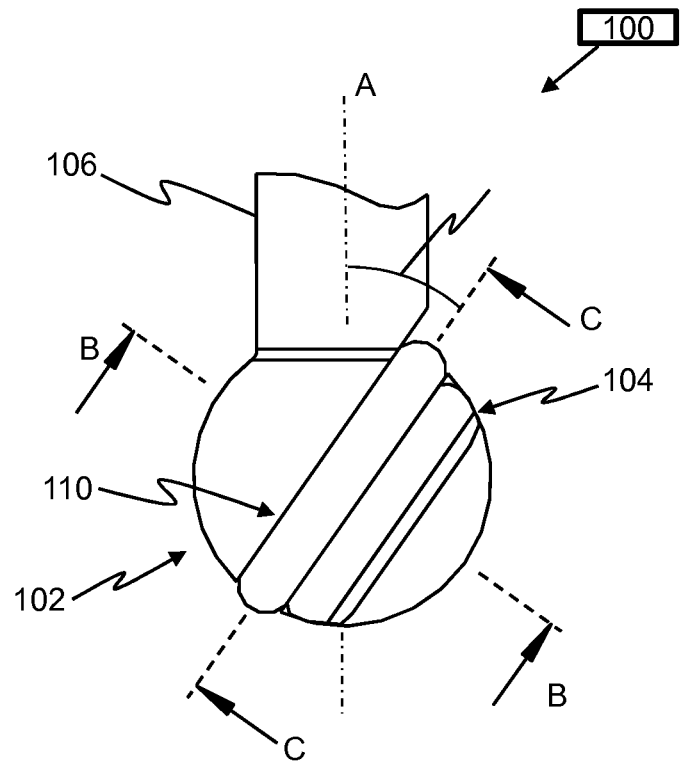

Referring to FIGS. 4 and 5, illustrated are rear and front views of the surgical burr 100, in accordance with an embodiment of the present disclosure. The surgical burr 100 comprises the working part 102 comprising at least one working means, such as the working means 104. Furthermore, the prevention means 110 is arranged on the working part 102. The working part 102 is attached to the shank 106. FIG. 5 also shows an angle α. Indeed, a plane of the groove is tilted at angle α as compared to axis of rotation A of the surgical burr.

Figure 6:
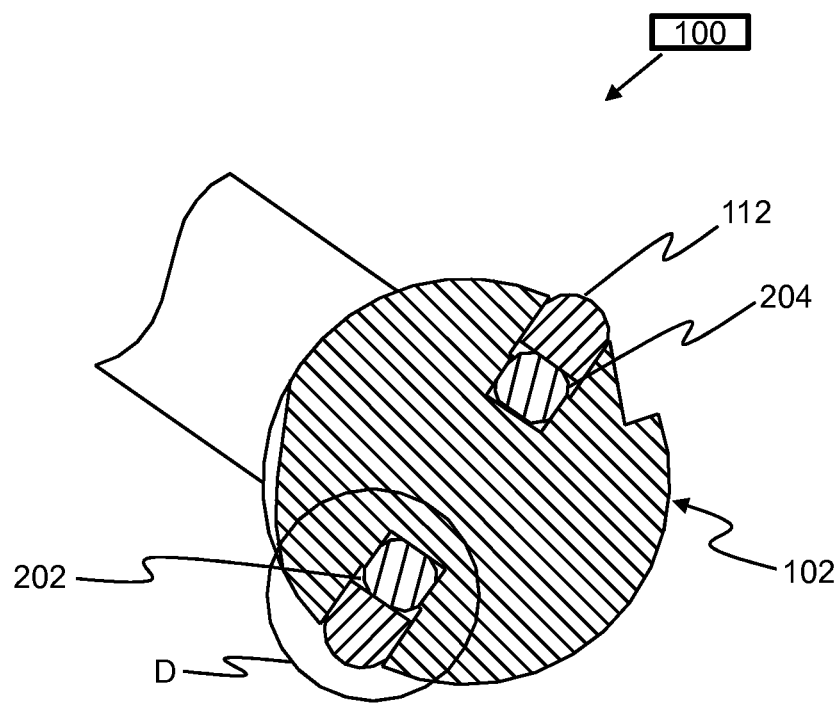
FIG. 6 is a cross-sectional view of the surgical burr of FIG. 5 along B-B', in accordance with an embodiment of the present disclosure.

Referring to FIG. 6, illustrated is a cross-sectional view of the surgical burr 100 of FIG. 5 along B-B', in accordance with an embodiment of the present disclosure. As shown, the surgical burr 100 includes an indentation 202 present along surface of working part 102 of the surgical burr 100. The indentation 202 includes a step shaped configuration. Further, the step shaped indentation 202 is shown to receive prevention means, particularly, an outer member 112 and an inner member 204, therein.

Figure 7:
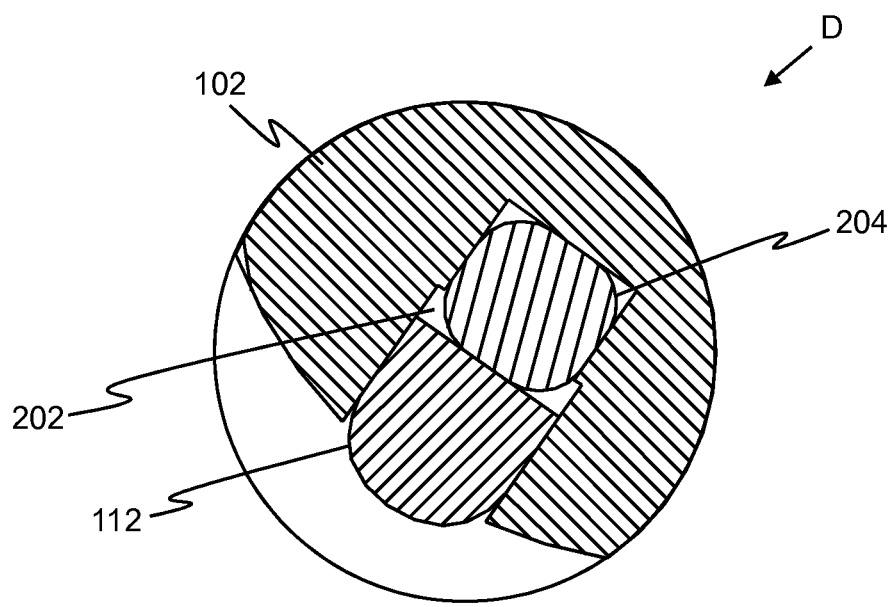
FIG. 7 is an enlarged view of an encircled section of the surgical burr of FIG. 6, in accordance with an embodiment of the present disclosure.

Referring to FIG. 7, illustrates is an enlarged view of an encircled section D of the surgical burr 100 of FIG. 6, in accordance with an embodiment of the present disclosure. As shown, the indentation 202 includes a stepped shape configuration shown to receive prevention means, particularly, an outer member 112 and an inner member 204, therein. Furthermore, the stepped shape configuration only allows limited radial movement of the outer member 112 related to the working part 102. In addition, the stepped shape configuration allows limited compression of the inner member 204.

Figure 8:
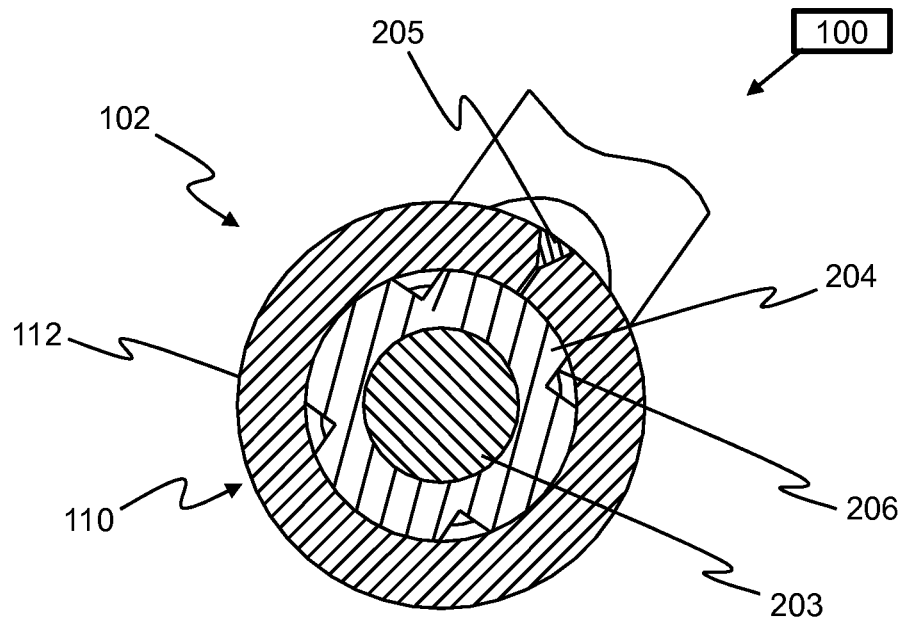
FIGS. 8, 9 and 10 are cross-sectional views of the surgical burr of FIG. 5 along C-C', in accordance with various embodiment of the present disclosure.
Figure 9:
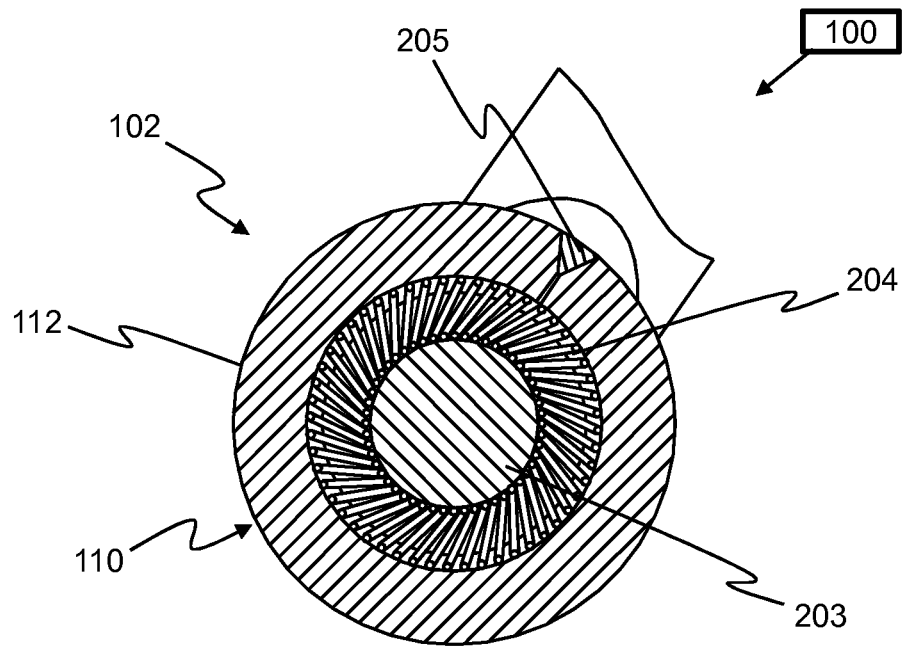
Figure 10:
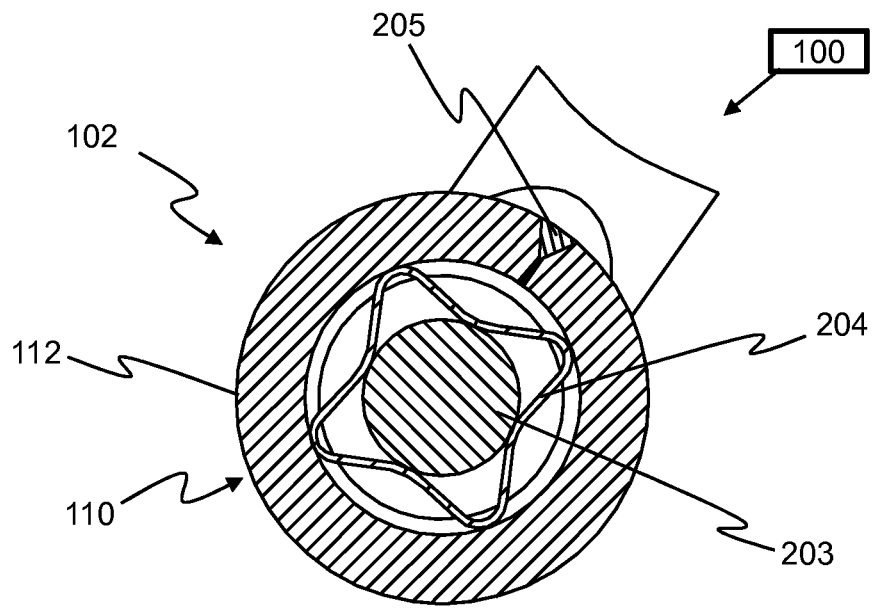

Referring to FIGS. 8, 9 and 10, illustrated are cross-sectional views of the surgical burr 100 of FIG. 5 along C-C', in accordance with various embodiment of the present disclosure. As shown, the surgical burr comprises a working part 102. Further, the working part 102 includes a prevention means 110. The prevention means comprises the outer member 112 and the inner member 204. As shown in FIG. 8, the inner member 204 is made of an elastomer. The inner member 204 is arranged in an indentation between the core 203 of the working part 102 and the outer member 112. Furthermore, the inner member 204 includes cuts 206 arranged on the outer surface of the inner member 204 to allow compression thereof. As shown in FIG. 9, the inner member 204 is a circular canted coil spring. Furthermore in FIG. 10, the inner member 204 is a circular wave spring. FIGS. 8, 9 and 10 also show a laser weld, indicated with reference number 205.

Figure 11:
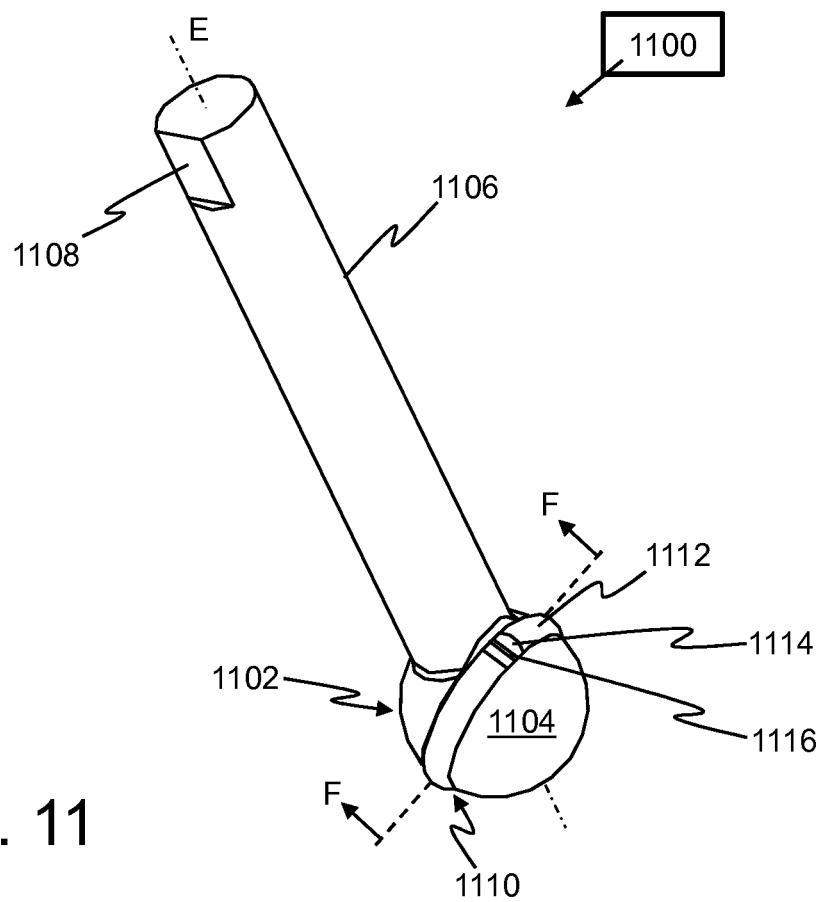
FIG. 11 is a perspective view of a surgical burr, in accordance with another embodiment of the present disclosure.

Referring to FIG. 11, illustrated is a perspective view of a surgical burr 1100, in accordance with an embodiment of the present disclosure. As shown, the surgical burr 1100 comprises a working part 1102 having at least one working means, such as a working means 1104. Furthermore, the working part 1102 is spherical in shape. The working part 1102 is attached to a shank 1106. The shank 1106 comprises attachment means 1108 at its other end, to allow the shank 1106 to receive the rotary motion. Further, the working part 1102 includes a prevention means 1110. Moreover, the prevention means 1110 includes an outer member 1112, such as a ring. The outer member 1112 includes an opening 1114 arranged to be in contact with a notch 1116 in the working part 1102. The surgical burr 1100 is a grinding burr and the working means 1104 is a working surface. Furthermore, the axis E illustrates the axis for rotational motion of the surgical burr 1100.

Figure 12:
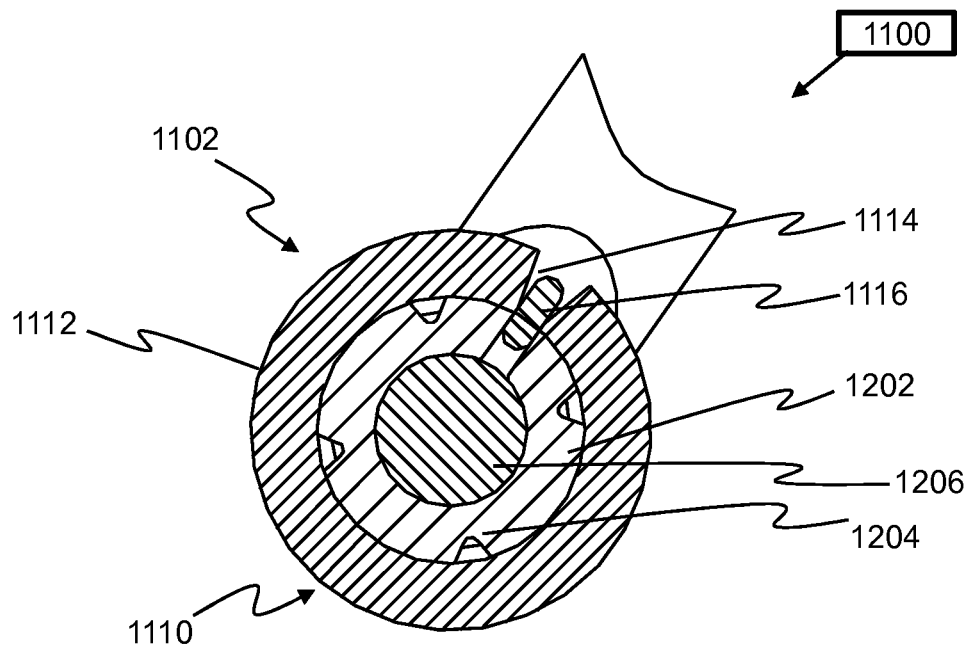
FIG. 12 is a cross-sectional view of the surgical burr of FIG. 11 along F-F', in accordance with an embodiment of the present disclosure.

Referring to FIG. 12, illustrated is cross-sectional view of the surgical burr 1100 of FIG. 11 along F-F', in accordance with an embodiment of the present disclosure. As shown, the prevention means 1110 includes the outer member 1112 and an inner member 1202. The inner member 1202 includes cuts 1204 on an outer surface of the inner member 1202. The inner member 1202 is arranged in an indentation between the core 1206 of the working part 1102 and the outer member 1112. Moreover, the notch 1116 is arranged to be in contact with the opening 1114 in the outer member 1112 of the prevention means 1110.

Figures 13, 14:
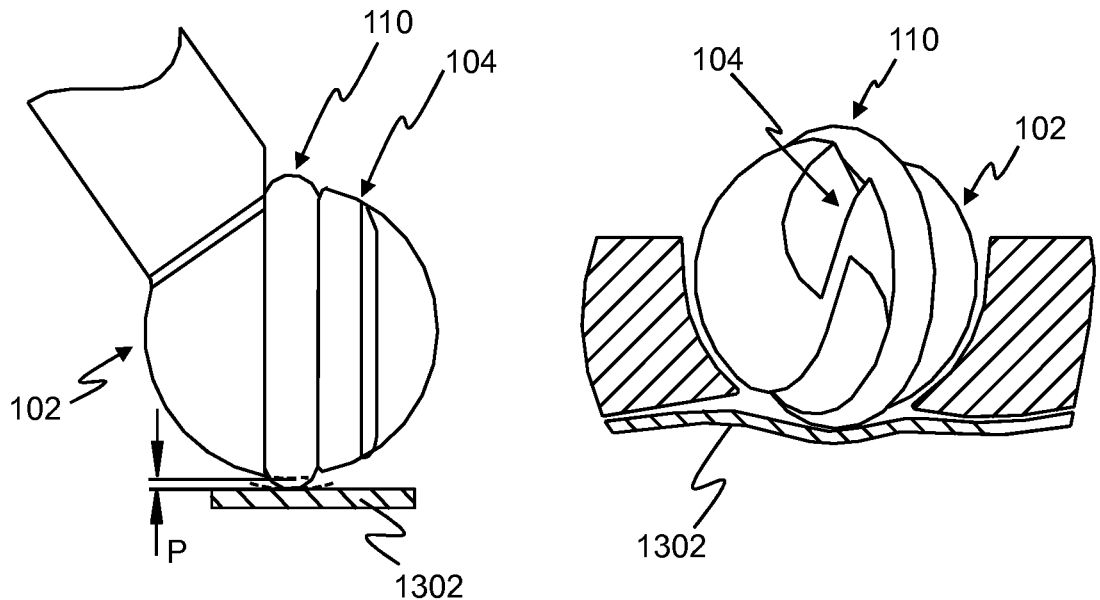
FIGS. 13, 14, 15 and 16 are schematic illustrations of the surgical burr of FIG. 1 in utilized states, in accordance with an embodiment of the present disclosure.

Referring to FIGS. 13 to 16, illustrated are schematic illustrations of the surgical burr 100 of FIG. 1 in utilized states, in accordance with an embodiment of the present disclosure. Optionally, the surgical burr 100 of FIG. 11 may be utilized in a similar manner. As shown, the surgical burr 100 includes the prevention means 110 and the working part 102, which working part 102 has a working means 104. The prevention means 110 is configured to protrude when a force applied to the prevention means 110 by a secondary material (such as soft tissue) 1302 (as shown in FIG. 14) is less than a predetermined amount of force. Therefore, the secondary material 1302 is not contacted by the working means 104 as shown by the distance P therebetween.

Figure 15:
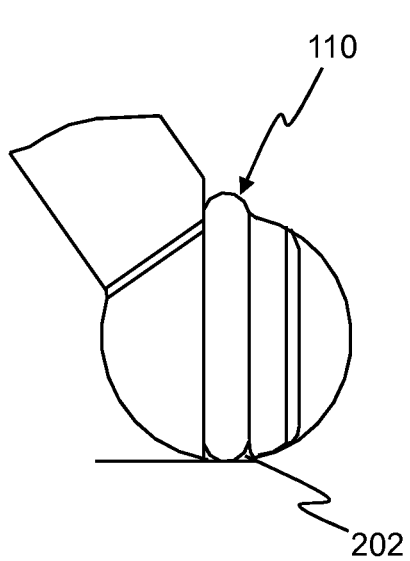
Figure 16:
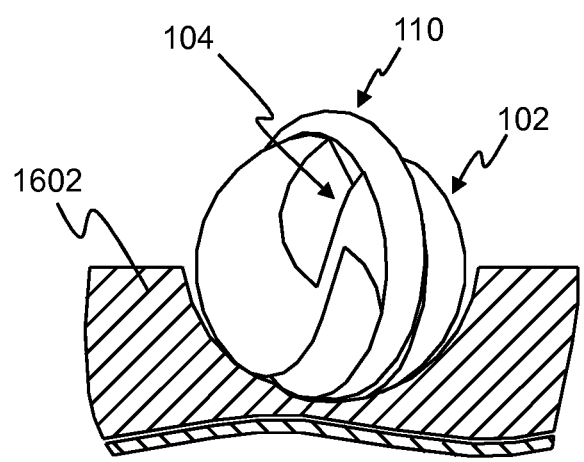

Referring now to FIGS. 15 and 16, the prevention means 110 is configured to retract to an indentation 202 when the force, applied to the prevention means 110 by a material (such as hard tissue) 1602 (as shown in FIG. 16), is equal or higher than a predetermined amount of force. This exposes the working means 104 of the working part 102 to the material 1602.

Figure 17:
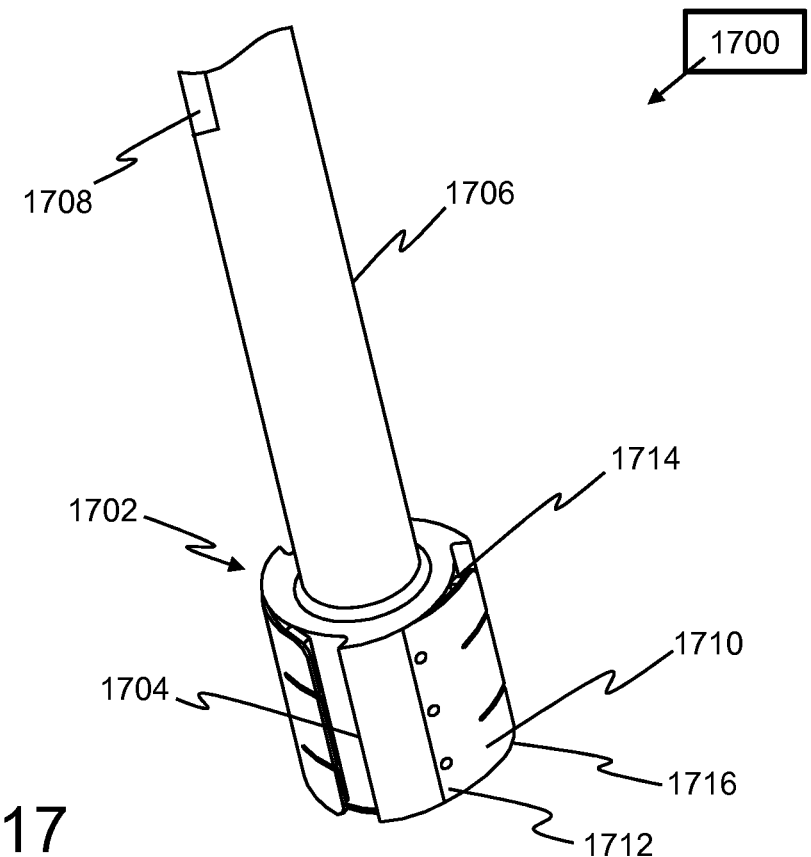
FIGS. 17, 18 and 19 are views of a surgical burr in accordance with an embodiment of the present disclosure.

Referring to FIG. 17, illustrated is a perspective view of a surgical burr 1700, in accordance with an embodiment of the present disclosure. As shown, the surgical burr 1700 comprises a working part 1702 having at least one working means, such as a working means 1704. Furthermore, the working part 1702 is cylindrical in shape. The working part 1702 is attached to a shank 1706. The shank 1706 comprises attachment means 1708 at its other end, to allow the shank 1706 to receive the rotary motion. Further, the working part 1702 includes resilient flaps as a prevention means, such as a resilient flap 1710. Furthermore, the resilient flaps, such as a resilient flap 1710, are attached to the working part 1702 from a first end 1712 thereof using spot welding, laser welding or an adhesive. Additionally, optionally, the resilient flaps, such as the resilient flap 1710, may have a filler, such as a filler 1714, attached to a second end 1716 of the resilient flap 1710. The surgical burr 1700 is a cutting burr and the working means 1704 are cutting edges.

Figure 18:
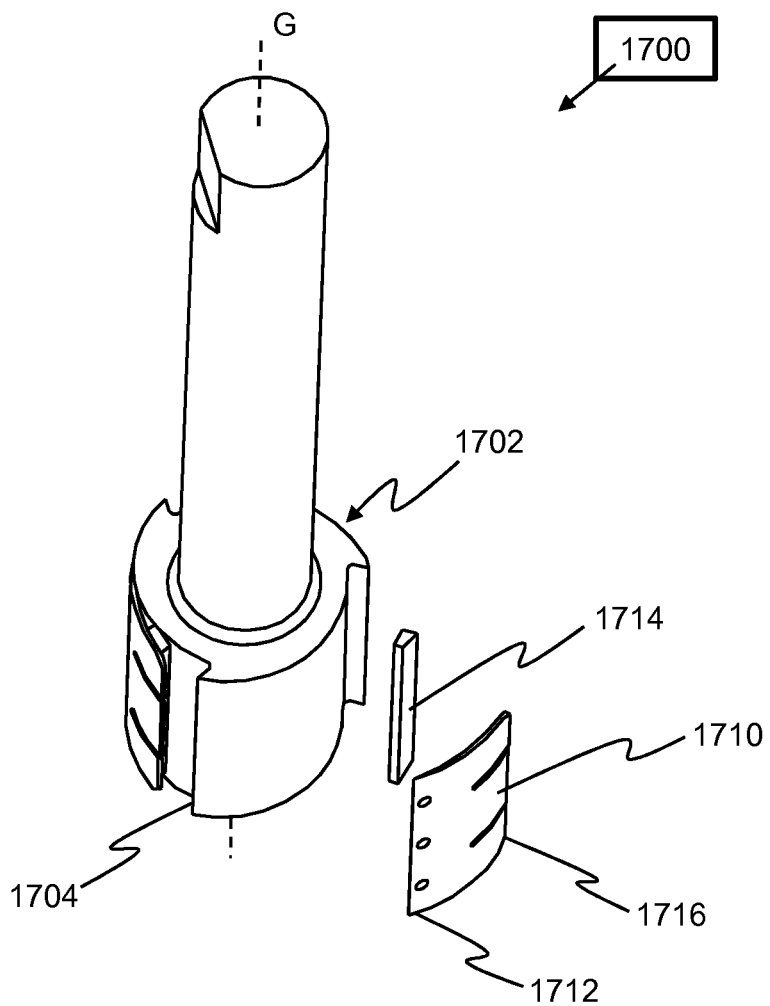

Referring to FIG. 18, illustrated is an exploded view of the surgical burr 1700, in accordance with an embodiment of the present disclosure. The working part 1702 of the surgical burr 1700 comprises cutting edges as working means 1704. Furthermore, the axis G illustrates the axis for rotational motion of the surgical burr 1700. Additionally, the surgical burr 1700 comprises resilient flaps as prevention means, such as the resilient flap 1710. The resilient flaps, such as the resilient flap 1710, are attached to the working part 1702 from a first end thereof, such as the first end 1712 of the resilient flap 1710. Furthermore, the filler, such as the filler 1714, is attached to the second end of the resilient flaps, such as the second end 1716 of the resilient flap 1710.

Figure 19:
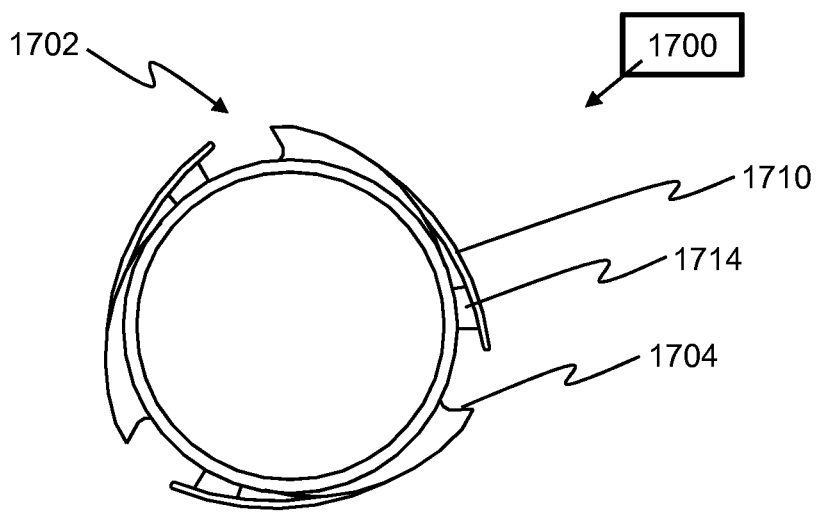

Referring to FIG. 19, illustrated is a bottom view of the surgical burr 1700, in accordance with an embodiment of the present disclosure. As shown, the working part 1702 comprises working means 1704, such as the cutting edges. Furthermore, the resilient flaps, such as the resilient flap 1710 is arranged on the working part 1702. Additionally, a filler, such as the filler 1714 is arranged between the resilient flaps, such as the resilient flap 1710, and the working part 1702.

Figure 20:
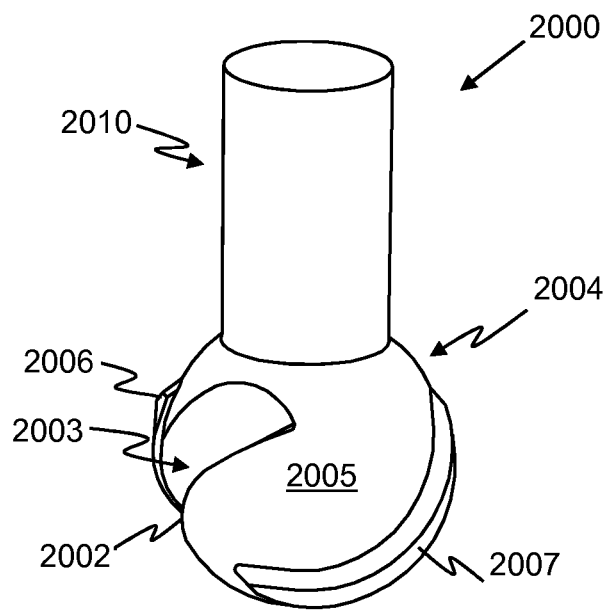
FIGS. 20 and 21 are perspective views of a surgical burr, in accordance with different embodiments of the present disclosure.
Figure 21:
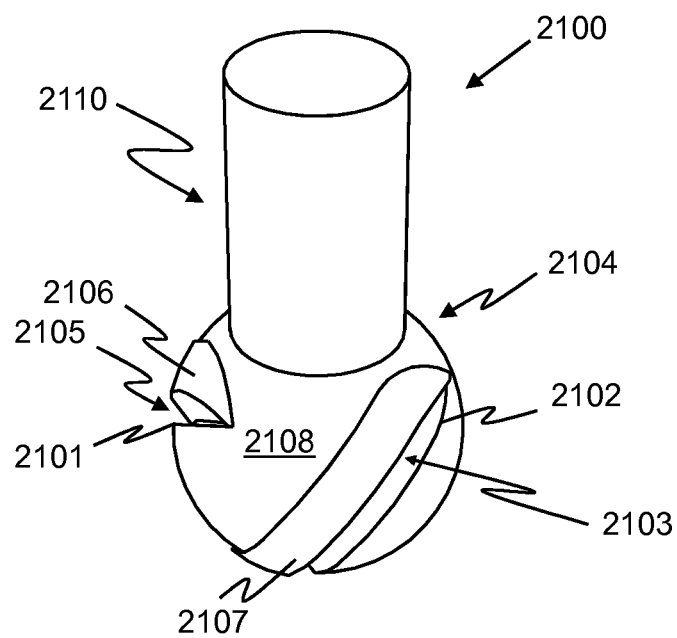

Referring to FIGS. 20 and 21, illustrated are perspective views of a surgical burr, in accordance with different embodiments of the present disclosure. As shown, a surgical burr 2000 includes a cutting edge 2002 in shape of flute 2003 as working means on the working part 2004 (having a working surface 2005) of the device 2000. The surgical burr 2000 includes prevention means, which includes a pair of elastomer segments 2006 and 2007 on opposite sides of a working part 2004 of the device 2000. The elastomer segments 2006 and 2007 are configured to protrude or retract depending upon the force applied thereto. Further, as shown in FIG. 21, a device 2100 includes cutting edges 2101 and 2102 in shape of flutes 2103 and 2105 on the working part 2104 (having a working surface 2108) of the surgical burr 2100. Further, the surgical burr 2100 also includes prevention means, such as elastomers 2106 and 2107 arranged in alternate flutes on the working part 2104. In addition, the devices 2000 and 2100 are shown to include attachment means 2010 and 2110, integral with the burrs, adapted to be operatively coupled to a rotating mechanism (not shown).

Figure 22:
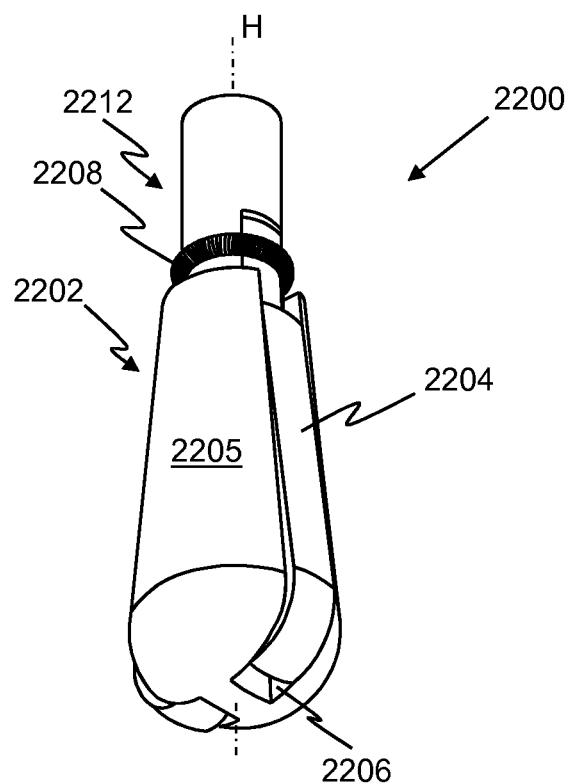
FIGS. 22 and 23 are different views of a surgical burr, in accordance with an embodiment of the present disclosure.
Figure 23:
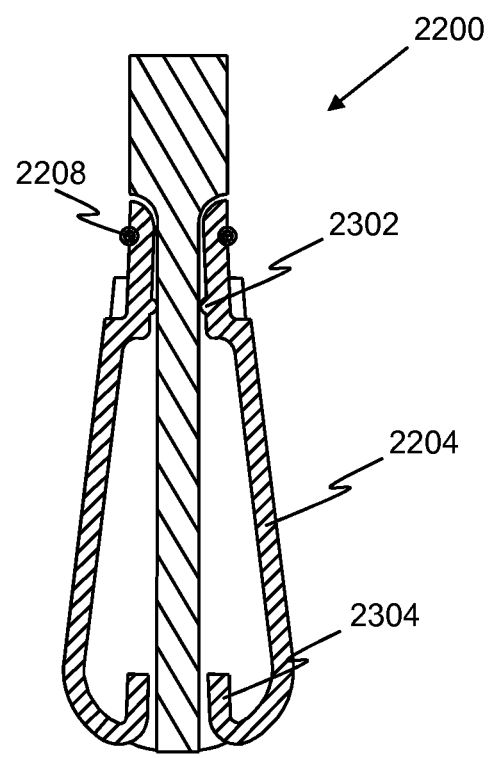

FIGS. 22 and 23 show yet another embodiment of a device according to the present disclosure. In FIG. 22, the device 2200 comprises a working part 2202 comprising a working surface 2205, prevention means 2204 and in indentation 2206 into which the prevention means 2204 may enter. Furthermore, the device comprises a shank 2212 and a spring 2208 for applying a force to the prevention means 2204. The rotation axis H of the device is also indicated. In FIG. 23, the device 2200 is shown as a cross-section from FIG. 22, and it can be seen that the prevention means 2204 has a hook shape 2304 at its end and a prominent part 2302 at its other end. The spring 2208 surrounds the shaft.

Figure 24:
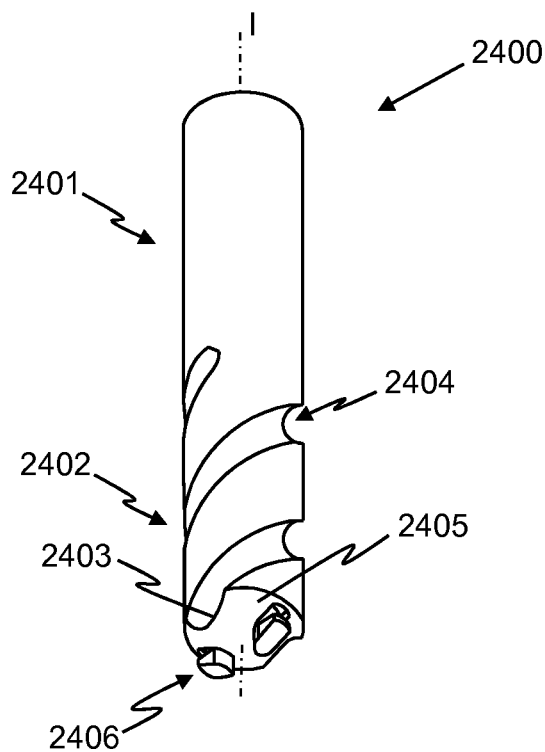
FIGS. 24 and 25 are different views of a twist-drill, in accordance with an embodiment of the present disclosure.

Referring to FIG. 24, illustrated is a perspective view of a twist-drill 2400, in accordance with an embodiment of the present disclosure. As shown, the device 2400 includes a working part 2402, having at least one working surface, such as the working surface 2405 having cutting edges 2403 and flutes 2404. The twist-drill 2400 also includes at least one prevention means, such as the prevention means 2406. In addition, the twist-drill 2400 is shown to include an attachment means 2401, integral with the drill bit, adapted to be operatively coupled to a drill device (not shown). The rotation axis I of the device is also indicated.

Figure 25:
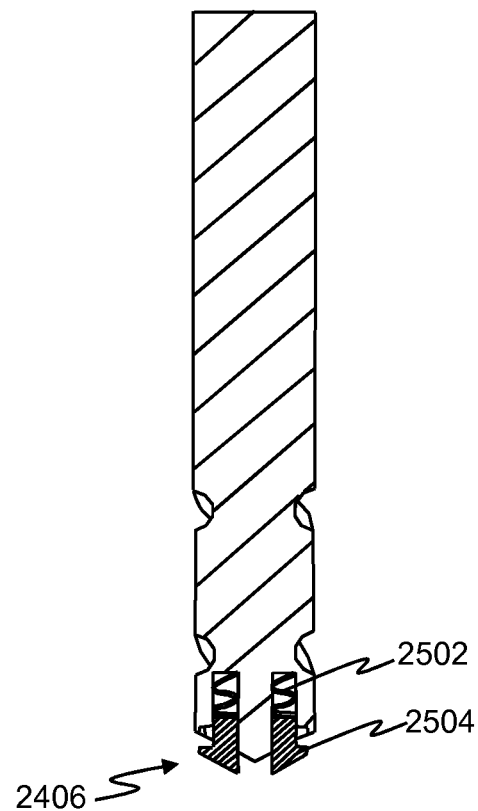

Referring to FIG. 25, illustrated is a cross-sectional view of the twist-drill 2400 of FIG. 24, in accordance with an embodiment of the present disclosure. As shown, an inner member 2502 of the prevention means 2406 is arranged between the working part (2402, as shown in FIG. 24) and an outer member 2504 of the prevention means 2406.

Figure 26:
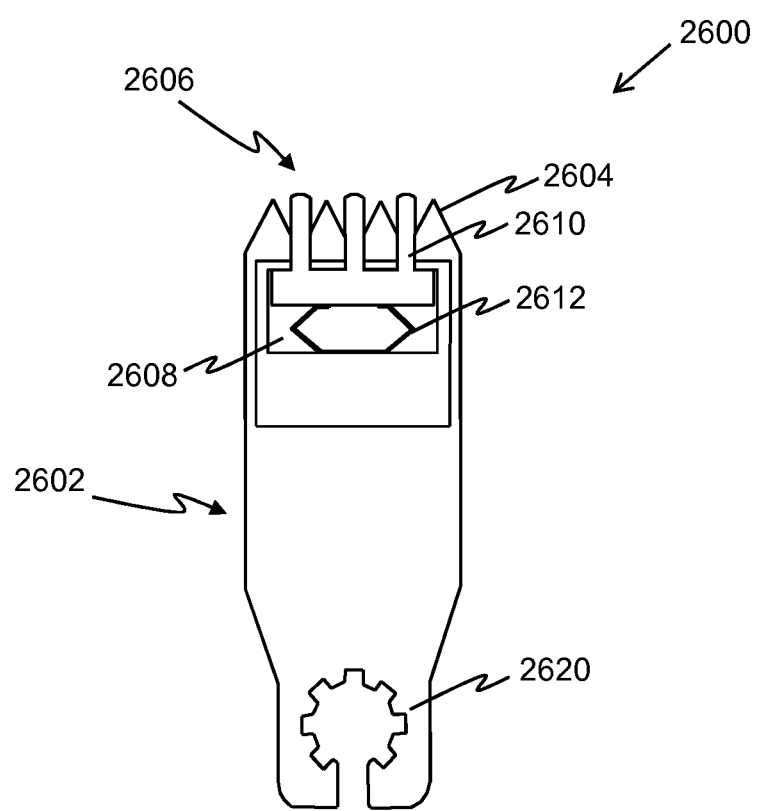
FIG. 26 is a front view of an oscillating saw blade, in accordance with an embodiment of the present disclosure.

Referring to FIG. 26, illustrated is a front view of an oscillating saw blade 2600, in accordance with an embodiment of the present disclosure. As shown, the oscillating saw blade 2600 includes a working part 2602 having working teeth 2604 as the working surface and prevention means 2606 arranged in an indentation 2608 present on a surface of the device 2600. The prevention means 2606 includes an outer member 2610 and an inner member 2612. The protrusion and retraction of the outer member 2610 is controlled by the inner member 2612 of the prevention means 2606. Also, the device 2600 is shown to include an attachment means 2620, integral with the oscillating saw blade, adapted to be operatively coupled to an oscillating mechanism (not shown).

Figure 27:
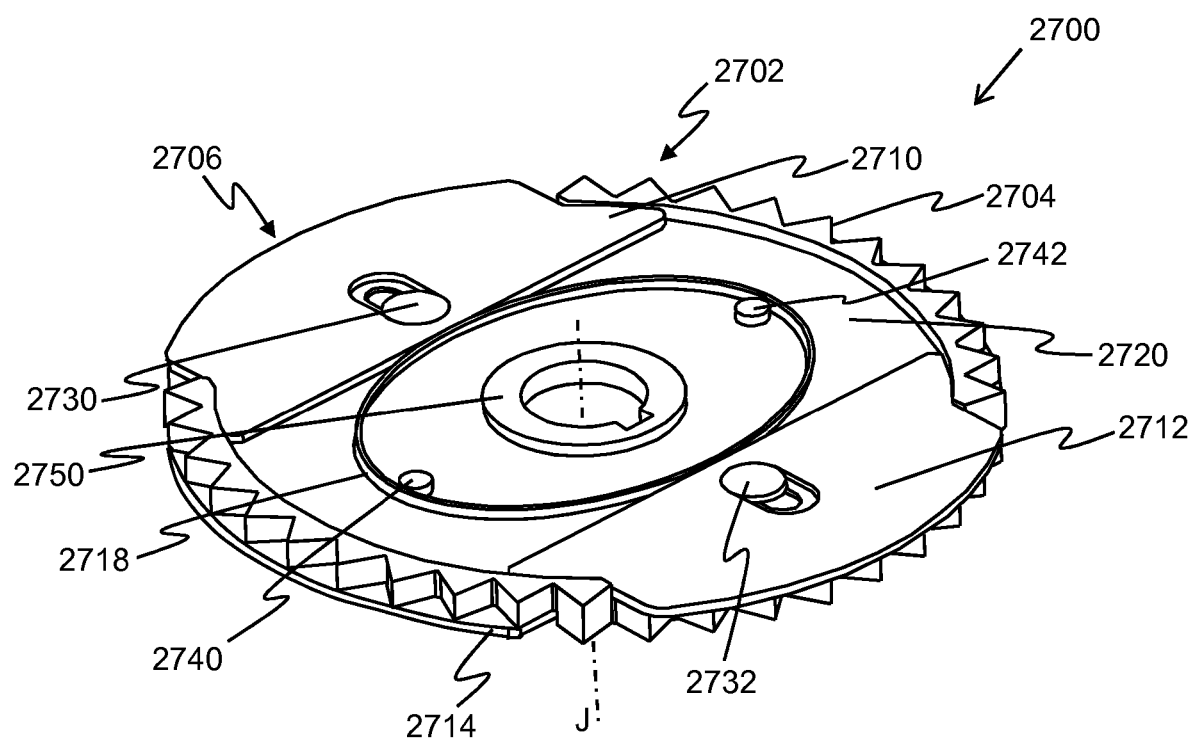
FIGS. 27 and 28 are different views of a saw, in accordance with an embodiment of the present disclosure.

Referring to FIG. 27, illustrated is a perspective view of a circular saw 2700, associated with a cutting disk, in accordance with an embodiment of the present disclosure. As shown, the saw 2700 includes a circular saw blade 2702 having working teeth 2704 as the working surface. The saw 2700 also includes prevention means 2706 on each side of the circular saw blade 2702. The prevention means 2706 includes two semi-circular outer members at each side of the circular saw blade 2702, depicted as outer members 2710 and 2712, and a common inner member 2718 arranged in an indentation 2720 on a surface of the circular saw blade 2702. The outer members 2710 and 2712 are supported with the help of support tabs 2730 and 2732, respectively. Further, the common inner members 2718 supported with the help of additional support tabs 2740 and 2742. Also, the saw 2700 is shown to include an attachment means 2750, integral with the circular saw blade 2702, adapted to be operatively coupled to a rotating mechanism (not shown). The rotation axis 3 of the device is also indicated.

Figure 28:
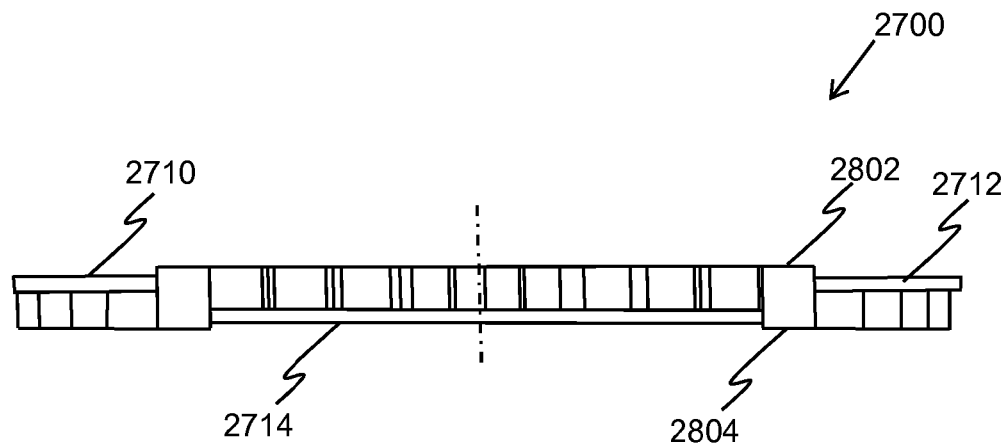

Referring to FIG. 28, illustrated is a side view of the saw 2700 of FIG. 27, in accordance with an embodiment of the present disclosure. As shown, the saw 2700 has two sides 2802 and 2804. Further, the outer members 2710 and 2712 are shown to be arranged on the side 2802, and an outer member 2714 is shown to be arranged on the side 2804.

Figure 29:
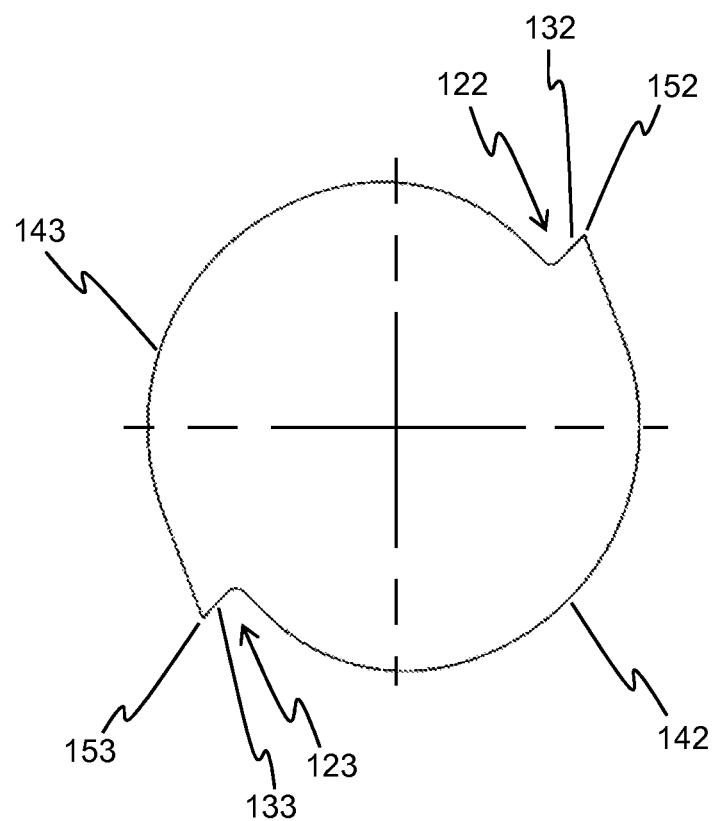
FIG. 29 is a cross-sectional view of a surgical round burr perpendicular to its central axis, illustrates rake and clearance surfaces.

Referring to FIG. 29, illustrated is a cross-sectional view of a surgical round burr perpendicular to central axis of the burr. The burr includes flutes 122 and 123 having rake surfaces 132 and 133 and clearance surfaces 142 and 143. The rake and clearance surfaces of each flute meet to form cutting edges 152 and 153 that extends along the length of the flute.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A surgical burr comprising
   prevention means;
   attachment means; and
   a working part comprising at least one working means for processing of a first material selected from a bone, a cartilage, a calcified tissue, a tooth and a foreign object within a patient body, wherein the working means is selected from a grinding surface and flutes defining cutting edges for removing material from the first material;
   wherein the prevention means encircles the working part and is arranged in an indentation in the working part and is configured to have:
      a first position in which it is arranged to at least partially prevent the working means from processing the first material, when a force applied to the prevention means is less than a predetermined amount of force, and
      a second position in which it is arranged to allow the working means to process the first material, when the force applied to the prevention means is equal to or higher than the predetermined amount of force;
   wherein the prevention means is arranged to protrude out from the indentation in the working part in its first position to prevent the working means from processing second material, adjacent to and softer than the first material, and to retract laterally into the indentation in the working part in its second position to allow the working means to process the first material; and
   wherein the prevention means comprises at least one outer member and at least one inner member.

2. A surgical burr according to claim 1, wherein the prevention means is arranged, in its first position, to push soft tissue away from the cutting edge, and, in its second position, to allow the working means to be in contact with hard tissue.

3. A surgical burr according to claim 2, wherein the indentation has a V-shape or a stepped shape profile.

4. A surgical burr according to claim 2, wherein
the working means are cutting edges; and
the prevention means comprises a number of flaps, each flap being arranged between two cutting edges,
wherein each flap is arranged, in its first position, to push soft tissue away from the cutting edge, and, in its second position, to allow the working means to be in contact with hard tissue.

5. A surgical burr according to claim 4, wherein
the working part has a cylindrical shape;
the cutting edges are arranged on the cylindrical surface.

6. A surgical burr according to claim 1, wherein the at least one inner member is made of an elastomer and between the working part and the at least one outer member.

7. A surgical burr according to claim 1, wherein the at least one inner member is a spring arranged between the working part and the at least one outer member.

8. A surgical burr according to claim 7, wherein the spring arranged between the working part and the at least one outer member is a circular canted coil spring or a circular wave spring.

9. A surgical burr according to claim 1, wherein the at least one outer member is a ring.

10. A surgical burr according to claim 9, wherein the ring has an opening arranged to be in contact with a notch in the working part for preventing the ring to rotate in relation to the working part.

11. A surgical burr according to claim 9, wherein the ring has a protrusion arranged to be in contact with a notch in the working part for preventing the ring to rotate in relation to the working part.

12. A surgical burr according to claim 1, wherein the prevention means has a form that conforms to the form of the working part when the prevention means is in its second position.

13. A surgical burr according to claim 1, wherein the predetermined amount of force is selected to prevent the processing of the second material.

14. A surgical burr according to claim 1, wherein the at least one outer member is rigid and the at least one inner member is resilient.

\* \* \* \* \*